United States Patent [19]

Taylor

[11] Patent Number: 5,118,913
[45] Date of Patent: Jun. 2, 1992

[54] CONTAINER AND REFERENCE ELECTRODE FOR USE IN RADIATED AQUEOUS ENVIRONMENTS

[75] Inventor: Dale F. Taylor, Schenectady, N.Y.

[73] Assignee: General Electric Company, Schenectady, N.Y.

[21] Appl. No.: 566,296

[22] Filed: Jul. 30, 1990

[51] Int. Cl.⁵ .................................... G01N 27/30
[52] U.S. Cl. .................... 204/435; 204/279; 204/286; 204/297 R; 204/400; 228/263.11; 228/263.12; 376/245; 376/256
[58] Field of Search ............ 204/286, 297 R, 400, 204/416–420, 435, 279; 376/245, 256

[56] References Cited

U.S. PATENT DOCUMENTS

| | | | |
|---|---|---|---|
| 2,190,835 | 2/1940 | Gruss et al. | 204/435 |
| 2,934,484 | 4/1960 | Anderson | 204/435 |
| 3,467,590 | 9/1969 | Gibson et al. | 204/435 |
| 3,853,731 | 12/1974 | Gray et al. | 204/420 |
| 4,177,126 | 12/1979 | Imaki et al. | 204/435 |
| 4,576,667 | 3/1986 | Taylor et al. | 156/89 |
| 4,882,029 | 11/1989 | Eickmann | 204/435 |
| 4,948,492 | 8/1990 | Niedrach et al. | 204/435 |

OTHER PUBLICATIONS

Vermilyea et al., *J. Electrochem. Soc.*, vol. 119, No. 1, (Jan. 1972), pp. 39–43.

*Primary Examiner*—T. Tung
*Attorney, Agent, or Firm*—James E. McGinness; James C. Davis, Jr.; James Magee, Jr.

[57] ABSTRACT

A container for electrochemical reactants for an electrode is provided, as well as electrodes employing the same. The electrodes can withstand the rigorous environment of a nuclear reactor core. The design of the container reduces stresses in the electrode and significantly improves its reliability. The container has a generally cylindrical member of an insulator. The member has a base region whose outer surface is a surface attachment region. The base region has an annular channel for a lead. The base region also has a generally conical cut-out. Sidewall means extend from said base to define a cavity for containing electrochemical reactants, e.g., silver chloride. A generally conical insert of an insulator mates with the cut-out. The outer surface of the insert, cut-out, and surface attachment region is metallized, and the insert is set in place by brazing. In the electrode the lead is in electrical contact with the apex of the insert.

20 Claims, 2 Drawing Sheets

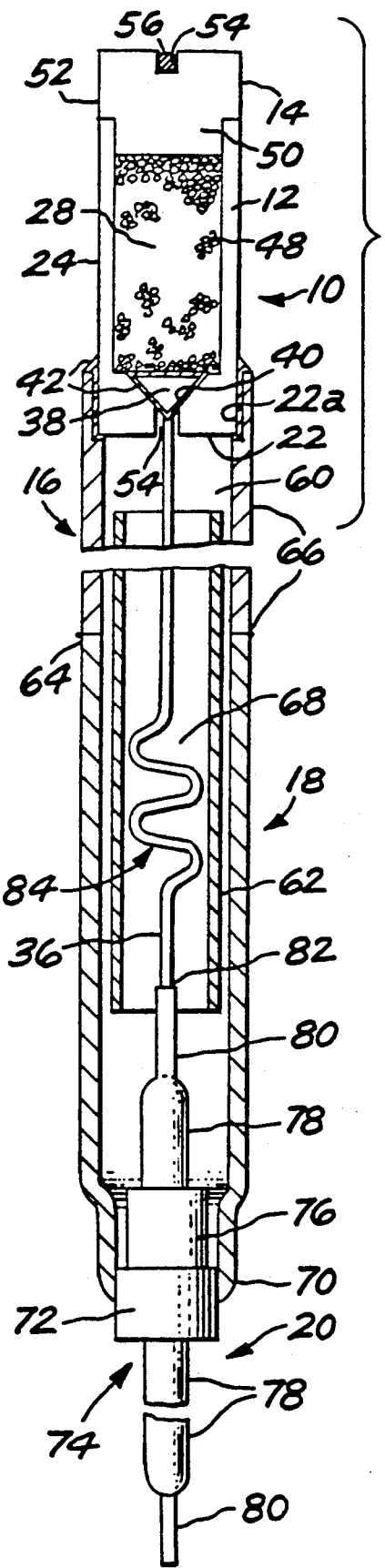
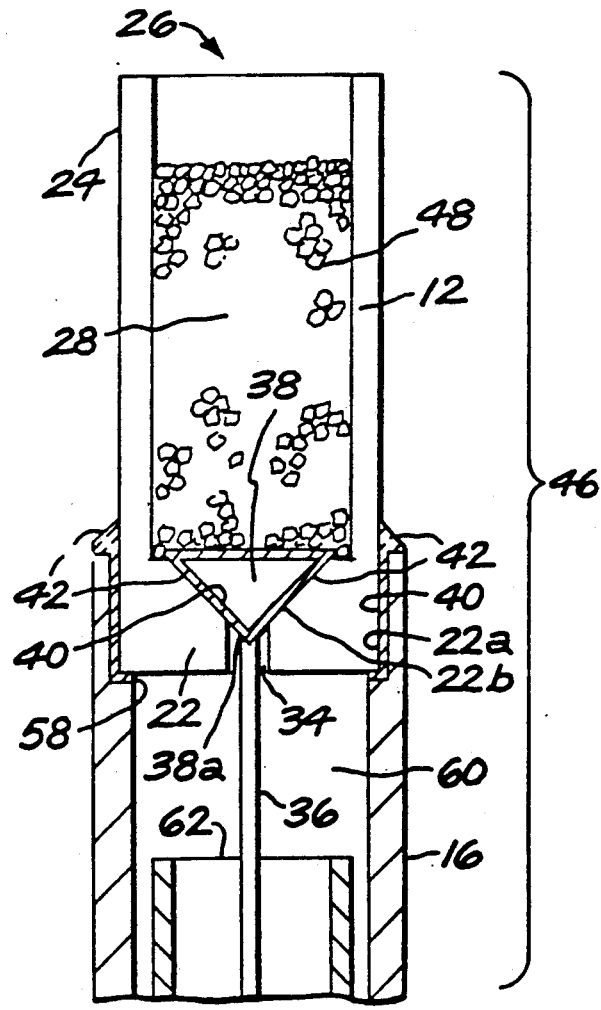

CONTAINER AND REFERENCE ELECTRODE FOR USE IN RADIATED AQUEOUS ENVIRONMENTS

This application is related to copending application Ser. No. 07/574,878, filed Aug. 30, 1990.

This invention relates to electrodes, particularly Ag/AgCl reference electrodes which consist of materials which do not degrade readily in a neutron flux and are therefore suitable for monitoring the coolant within a nuclear reactor.

BACKGROUND OF THE INVENTION

The nuclear power industry long has been engaged in a multitude of studies and investigations seeking improvement in the stamina and reliability of the materials and components forming a reactor-based power system. One such investigation has been concerned with intergranular stress corrosion cracking which heretofore principally has been manifested in the water recirculation piping systems external to the radiation intense reactor core regions of nuclear facilities. Typically, the piping architecture of these external systems is formed of a stainless steel material.

Generally, the studies referred to above have determined that three factors must occur in coincidence to create conditions that promote intergranular stress corrosion cracking. One factor is a sensitization of the metal such as stainless steel, for example, by chromium depletion at grain boundaries. Chromium depletion at grain boundaries may be caused by heat treatment in the course of normal processing of the metal or by welding and like procedures. A second factor is the presence of tensile stress in the material. A third factor is the oxygenated normal water chemistry environment typically present in a boiling water reactor. This latter environment is occasioned by any of a variety of oxidizing and corrosive species contributed by impurities in reactor coolant water. An electrochemical potential monitoring approach has been combined with controlled additions of hydrogen into the coolant to monitor and control the oxygenated environment factor.

Electrochemical potential monitoring is carried out employing paired electrochemical half-cell probes or electrodes which are mounted within the recirculation piping and accessed to the external environment through gland type mountings or the like. Where, as in the instant application, the electrode system of interest involves a metal-metal ion couple, then the reference electrode can conveniently be a metal-metal insoluble salt-anion electrode. A suitable reference electrode may be based, for example, on the half-cell reaction between silver and silver chloride. Calibration of the cell defining electrode pair is carried out by appropriate Nernst based electrochemical calculations, as well as by thermodynamic evaluation in combination with laboratory testing within a simulated environment against a standard electrode.

Half-cell electrodes capable of operation in high pressure and high temperature fluids have been developed for for use in reactor recirculation piping. For example, see U.S. Pat. No. 4,576,667. Such reference electrodes have combined metal housings, ceramic members, and polymeric sealing means formed, for example, from polytetrafluoroethylene or Teflon synthetic resin polymers, to provide electrical isolation of a silver electrode within the reference electrode. These structures have performed adequately in the more benign and essentially radiation free environments of, for example, recirculation piping in nuclear reactors.

Over the recent past, investigators have sought to expand the reference electrode monitoring procedures to the severe environment of the fluid in the vicinity of the reactor core itself for the purpose of studying and quantifying the effect of corrosive species on stress corrosion cracking. Within the reactor core, reference electrodes can be mounted in specially designed small cross section tubing. Such tubing is located among the fuel elements in the reactor core, and is used to house various monitoring devices, such as neutron detectors. As a result, these tubes are known as local power-range monitor tubes.

Thus, the reference electrodes are located in the severe environment of the fluid in the reactor core having a typical high temperature of 274° C., pressure of 1,000 psi, and radiation of $10^9$ rads per hour gamma and $10^{13}$ rads per hour neutron. Reference electrode structures of earlier designs are completely inadequate for this reactor core environment, both from a material standpoint, and with respect to the critical need to prevent leakage of radio-active materials to the ambient environment of the reactor. For example, the polymeric seals used in reference electrodes cannot withstand intense radiation with the result being failure of the electrode and leakage of radioactive materials. In known reference electrodes, leakage at the polymeric seal can cause failure due to electrical shorting between a lead wire within the electrode, and the test environment, i.e., the reactor coolant. An electrode which does not suffer from these deficiencies of prior electrodes would therefore be desirable.

SUMMARY OF THE INVENTION

The present invention provides a reference electrode which has a structure particularly suited for employment within the rigorous environment of the reactor core of a nuclear power facility. The reference electrode is configured so that the ambient pressure of the coolant acts upon the container structure of the electrode to reduce tensile stress at a brazed seal between ceramic members, thereby imparting improved reliability to reference electrodes of this invention. In particular, the reference electrode of this invention is able to withstand high intensity nuclear radiation and high pressure reactor water as well as high temperatures.

Thus, the present invention provides a reference electrode comprising a generally cylindrical container of an insulator, said container having a base region with an externally disposed surface attachment region and sidewall means extending to an access opening therefrom for defining an internally disposed cavity. Means defining a generally conical cut-out in said base region, and a generally conical insert of an insulator that mates with said conical cut-out. The insert, cut-out, and surface attachment region of the base are metallized on their outer surfaces. The conical insert is set in place in said conical cut-out by silver brazing, and a silver-salt electrochemical reactant is located within said cavity. Cap means formed of an insulator is positioned over said container opening for retaining the silver-salt electrochemical reactant within said cavity while permitting electrolytic communication with environment outside said cavity. A sleeve means is formed of a first select metal exhibiting a coefficient of expansion compatible with said insulative material of said container and has an acceptance portion for an intimately sealed brazed connection with said container surface attachment region and has an internal channel extending along the lengthwise extent thereof. A lead connected in electrical contact with the conical insert insulatively extends from the base and through said internal channel. Positioning and signal transfer means operatively support said sleeve means and convey electrical signals from said lead.

After positioning in a nuclear reactor, ambient pressure from coolant surrounding the reference electrode applies pressure to the conical insert pressing the insert against the mating conical cut-out so that the braze therebetween is a compressed sealing braze that provides added life to the electrode. Thermal expansion differences between the silver braze and the ceramic insert result in tensile stresses that cause silver brazes to lose adherence to ceramic surfaces. However, the compressive force acting upon the braze helps to offset the tensile force and retains the integrity of the seal.

The present invention also provides a container for electrochemical reactants for an electrode comprising, a generally cylindrical member of an insulator, said member having a base region with an externally disposed surface attachment region and sidewall means extending to an access opening therefrom for defining an internally disposed cavity for containing said electrochemical reactants, means defining a generally conical cut-out in said base region that extends through the base, and a generally conical insert of an insulator that mates with said generally conical cut-out, said insert, cut-out, and surface attachment region being metallized, and said conical insert being set in place in said generally conical cut-out by silver brazing.

Other objects of the invention will, in part, be obvious and will, in part, appear hereinafter.

The invention, accordingly, comprises the apparatus possessing the construction, combination of elements, and arrangement of parts which are exemplified in the following detailed disclosure. For a fuller understanding of the nature and objects of the invention, reference should be made to the following detailed description taken in connection with the accompanying drawings.

BRIEF DESCRIPTION OF THE DRAWINGS

FIG. 1 is a partial sectional view of an electrode according to the invention;

FIG. 2 is an enlarged sectional view of a portion of the electrode of FIG. 1.

DETAILED DESCRIPTION

Figure 3:
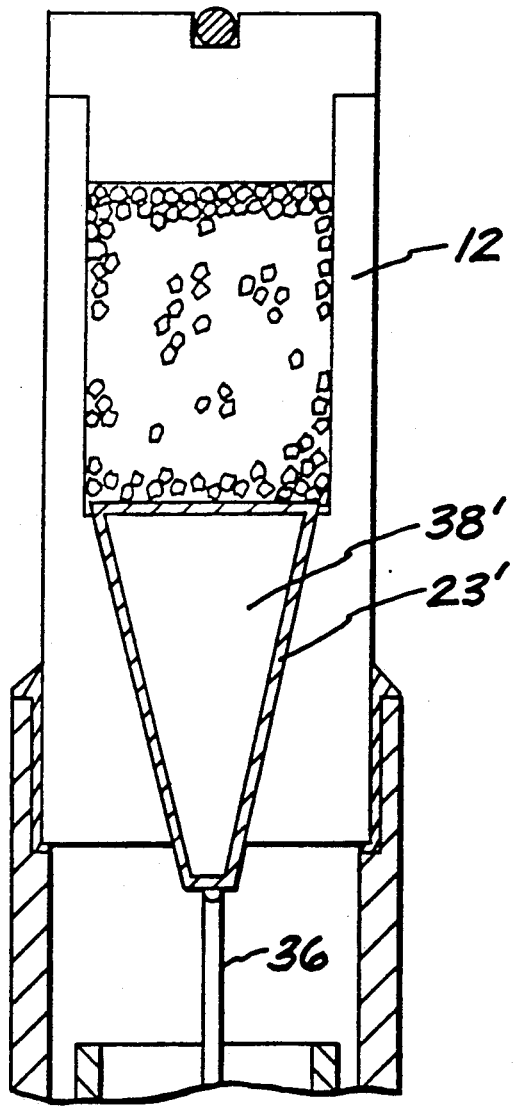
FIG. 3 is an enlarged sectional view of a separate embodiment of the electrode portion shown in FIG. 2.

While having utility in a broad variety of industrial monitoring functions, the electrode structure of the instant invention finds particular utility operating in the rigorous environment of the reactor core of a nuclear power facility. No elastomeric seals or polymeric components are present in its structure. Rather, a brazed and welded assembly consisting only of ceramic and metal parts forms the structure of the device. The metal and ceramic parts are designed in a manner to be brazed together so that the brazed connections provide a reliable seal from the high pressure and high temperature coolant. Such brazed connections are used to replace the polymeric seals used in known reference electrodes.

We have found that not all brazed connections between ceramic members, or metal and ceramic members, provide a reliable seal from the high pressure and high temperature coolant in a nuclear reactor. For example, one problem to be overcome with a brazed connection between a silver electrode and a ceramic member, to provide electrical isolation of the silver electrode, is the thermal expansion miss match of the braze material on the ceramic. The thermal expansion difference between the braze material and the ceramic material causes tensile forces to develop in the braze material so that the braze delaminates from the ceramic and the high pressure and high temperature coolant passes through the brazed connection and shorts out the electrode.

The electrode of this invention finds preferable employment as a reference component of an electrode system involving a metal-metal ion couple and thus the instant electrode can conveniently be a metal insoluble salt-anion electrode, for example, silver salts such as silver bromide, silver iodide, and preferably silver chloride. For the embodiment shown, the device is a silver-silver chloride reference which functions reversibly. In general, these electrodes consist of a silver metal with silver chloride immersed in a solution containing chloride anions. The electrode reaction is:

$$AgCl(s) + e^- \rightleftharpoons Ag(s) - Cl^-.$$

At 25° C. the collector electrical potential of such an electrode can be computed as: 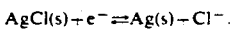.

For a more detailed discussion in connection with the above, reference is made to "Physical Chemistry" by G. W. Castellan, Chapter 17, "Equilibria in Electrochemical Cells", pp. 344-382, Addision-Wesley Publishing Co., Reading, Mass. (1964).

Referring to FIG. 1, the structure of the reference electrode according to the invention is represented in general at 10 in sectional fashion. Device 10 has a generally cylindrical structure comprised of components including a cylindrically shaped container 12, a cylindrical cap 14 inserted into container 12, a sleeve 16 which supports container 12, and a conical insert 38 positioned in the base of container 12. Insert 38 is preferably made of alumina, and most preferably sapphire, and has metallization 40 on its exterior. Insert 38 is set in place by a silver braze 42, the metal component of the half-cell. Silver braze 42 is also used as the seal between container 12 and sleeve 16. Insert 38, at metallization 40 contacts lead 36 which runs through channel 34 of container 12. Device 10 further comprises an elongate cylindrical transition piece 18 and a cable assembly or connector 20. A Silver chloride metal-salt 48 is within container 12.

Container 12 is structured not only to withstand the duress otherwise imposed by radiation, high temperatures, and pressure, but also to achieve a highly reliable seal to avoid the incursion of reactor coolant water through the electrode and ultimately to the outside environment. Container 12, in its preferred embodiment, is formed of sapphire which is a single crystalline form of alumina. The sapphire material, not only provides a requisite electrical insulation but also, by virtue of its single crystalline structure, is highly resistant to attack by water within which it is immersed. Thus, there is no intergranular penetration into the material, even though there will be some general corrosion attack. Accordingly, the material forming container 12 is ideal for the contemplated environment. Other materials will occur to those art skilled, for example high purity alumina, zirconia, or ruby.

Referring to FIG. 2, container 12 is formed having a cylindrical base region 22 from which a cylindrically shaped wall 24 extends to an end surface or access opening 26. The walls 24 define an internally disposed cavity 28 within which is disposed metal-salt 48. Cylindrical base region 22 is formed with a channel 34 to accommodate lead 36. Cylindrical base region 22 is also formed with a conical cut-out 22b to accommodate insert 38. The conical cut-out 22b can be formed by grinding cylindrical base region 22; and channel 34 can be formed by drilling a hole.

Another suitable conical insert is shown in FIG. 3. Conical cut-out 23' extends through the base region of container 12. Conical insert 38' extends and protrudes beyond conical cut-out 23'. The conical insert in the base region of the container provides a brazed compressive seal between ceramic components because of the action of the high pressure coolant. Therefore, it is only required that the conical insert provide a compressively sealed braze between the ceramic components to provide additional protection to the lead 36.

Referring to FIG. 2, to achieve a sealed union of high integrity between insert 38 and the surface of the conical cut-out 22b, a metallized seal of the type known as the sintered metal powder process is made on the ceramic surfaces. A paint containing metal powders such as molybdenum or tungsten, and sometimes containing glass forming or modifying oxides such as $SiO_2$ or MnO is applied to the insert and conical cut-out and fired in a wet hydrogen atmosphere having dew points in the $-5°$ C. to $+20°$ C. range to sinter the coating. A glassy phase having a mixture of glass and crystalline phases forms a tightly adherent seal on the ceramic insulator. Further explanation of the sintered metal powder process can be found in "Material and Techniques for Electron Tubes" by W. H. Kohl, Reinhold Publishing Corp., N.Y. 1960, pp. 488-493, which is incorporated by reference herein.

The fired surface is inspected and the thus-metallized region is nickel-plated and heated to sinter the metallized layer and nickel plating. The sintered surface is then inspected and silver plated. The inspections are performed to assure the continuity of the platings. This surface treatment 34 prepares the insulator for acceptance of a silver braze bond. The thus-metallized or plated insert 38 is set into the metallized or plated conical cut-out 22b of cylindrical base region 22 of container 12 by silver braze 42.

Lead 36 may be formed of platinum, iridium or Kovar; Kovar materials are a group of alloys, e.g., Fe 53.8%, Ni 29%, Co 17% and Mn 0.2%, which exhibit a coefficient of thermal expansion characteristic compatible with that of the alumina or other materials suitable for container 12. Lead 36 can be brazed to plated insert 38 at the apex or tip thereof 38a. Container 12 is set in place in sleeve 16 by braze 42. Sleeve 16 is also preferably of Kovar.

Shown positioned within cavity 28 of the retainer 12 is a deposit of silver chloride which herein is shown schematically in granular form as an aqueous suspension as represented at 48. In a preferred arrangement, the silver chloride may be melted and formed into rods, portions or plugs of which then may be located within cavity 28.

Referring back to FIG. 1, end cap 14 is also preferably formed of sapphire, the single crystalline form of alumina and may, for example, be fashioned of the noted alternate materials. Cylindrical in general form, the cap 14 is seen having a neck component 50 which is integrally formed with a top flange region 52. The cap is dimensioned so as to provide a "tight" fit over access opening 26, from FIG. 2, and with the cylindrical interior surface of the cavity 28. The noted fit of the cap 14 to the container 12 is one which permits electrolytic communication with the reactor core water with a very minimum movement or mass transfer of water or material. In effect, a diffusion junction is found between the cap and the wall of the container. Exemplary of the type of fit involved, the access opening diameter at container 12 may, for example, be machined to provide a diameter of 0.235 inch with a tolerance of $+0.001$, $-0.000$, while the corresponding diameter of the neck component 50 at cap 14 may be machined with a diameter of 0.235 inch under tolerances of $+0.00$, $-0.001$ inch. Further retention of the cap 14 is provided by a transverse slot 54 within which a stainless steel wire, shown in section at 56, is positioned thereabout in harness fashion and attached at the lower connector 20 region of device 10.

Referring to FIG. 2, container 12 of device 10 is initially supported by the cylindrical crucible sleeve 16 which, to achieve compatibility with sapphire container 12 from the standpoint of the thermal coefficient of expansion thereof, is preferably formed also of Kovar. The internal diameter of the sleeve 16 is offset, for example, by counterboring at 58 to provide an acceptance portion suited for receiving and being attached to the surface attachment region 22a of base region 22 of container 12 for forming an intimate seal thereat. The initially produced cylinder of Kovar for sleeve 16 is prepared by initially cleaning and inspecting it, following which a post machine annealing procedure is carried out. Following this annealing procedure, the component is nickel-plated and that nickel-plating is sintered, following which it is inspected. A second nickel-plating and sintering procedure then is carried out, followed by a next inspection. Generally, the thus-prepared component is stored in sealed plastic packaging until it is utilized.

Surface attachment region 22a of container 12 is metallized by the same procedure described above for metallizing insert 38 and conical cut-out 22b. An intimate compressive seal of the metallized surface attachment region 22a of container 12 with the acceptance portion 58 of sleeve 16 is provided by silver brazing 42. This arrangement then completes a highly secure seal for electrode 10 as is required in view of the intended use thereof within the environment of a nuclear reactor core. The hollow interior 60 of cylindrical sleeve 16 provides an internal channel through which the conductor lead 36 may pass. To assure that lead 36 is insulated from the internal surfaces of sleeve 16, a tube 62 can be inserted within channel 60. Annular tube 62 can be of ceramic or alumina to provide insulation while remaining immune from the temperatures encountered with the intended use of device 10.

Kovar sleeve 16 is supported, in turn, by attachment to the cylindrical transition component 18 which, for the instant application may be formed of a type 304 stainless steel. The transition piece 18 is of corresponding diametric extent as sleeve 16 and is attached at its transition end 64 to the corresponding attachment surface 66 thereof utilizing a tungsten inert gas weld (TIG) as applied, for example, by a tube welder. The hollow interior 68 of transition tube 18 provides an internal channel representing a continuation of the channel 60 of sleeve 16. Tube 62 is seen to extend continuously thereinto. The lower end of transition tube 18 is formed in necked down fashion to provide a sealing end 70. End 70 is welded, such as by the noted tungsten inert gas welding technique, to the cylindrical stainless steel collar 72 of a cable connector assembly represented generally at 74 and which is shown having a ceramic support component 76 through which a mineral insulated cable 78 extends. Cable 78 may be provided having a stainless steel outer shell within which the noted mineral insulation may be provided as alumina and centrally disposed within which is a conducting cable 80. The mineral insulated cable 78 extends outwardly to the ambient environment from the reactor core region in the application of interest. To provide an electric circuit completing connection with cable 80, lead 36 is spot welded thereto at 82. To facilitate this attachment and provide a modicum of tension with the lead 36, a spring winding is formed in lead 36 as represented in general at 84. Cable assembly 74 is marketed, for example, by Reutor-Stokes, a division of General Electric Company, Twinsburg. Ohio.

Area 46 of FIG. 1 is shown in an enlarged view in FIG. 2. In FIG. 2, container 12, sleeve 16, brazes 42, insert 38 and metallized surface attachment region 2a are depicted in greater detail. The design of the present electrode, especially as shown in enlarged detail in FIG. 2 benefits from the ambient pressure differential between the coolant in a nuclear reactor core and the inside of the electrode. The conductivity of the braze metal eliminates the requirement for a second metal in the vulnerable inner chamber of the electrode. The conical configuration of insert 38 maintains a uniform ceramic/ceramic gap with vertical displacement of the insert. The optimization of the diameter/depth/contact angle of the insert is within the ambit of the skilled artisan from this disclosure. Ambient pressure from the coolant helps reduce tensile stress at the ceramic/silver interface due to the conical shape of the insert and the matching conical cut-out in the base region. The external Kovar sleeve 16 provides a compressive brazed seal between container 12 and sleeve 16. Reduction of the tensile stress between ceramic members and braze materials in this way significantly improves the reliability of reference electrodes of the present invention. Reference electrodes of the present invention are useful for monitoring electrochemical potentials.

Having thus described in detail preferred embodiments of the present invention, it is to be understood that the invention defined by the appended claims is not to be limited by particular details set forth in the above description as many apparent variations thereof are possible without departing from the spirit or scope of the present invention.

What is claimed:

1. A reference electrode comprising:
   a generally cylindrical container of an insulator, said container having a base region with an externally disposed surface attachment region and sidewall means extending to an access opening therefrom for defining an internally disposed cavity, means defining a generally conical cut-out in said base region that extends through said base region,
   a generally conical insert of an insulator that mates with said generally conical cut-out, said insert, cut-out, and surface attachment region being metallized for acceptance of a silver braze, said generally conical insert being set in place in said conical cut-out by a silver braze,
   a silver-salt electrochemical reactant located within said cavity,
   cap means formed of an insulator and positioned over said container opening for retaining and silver-salt electrochemical reactant within said cavity while permitting electrolytic communication with environment outside said sleeve cavity,
   sleeve means formed of a select metal exhibiting a coefficient if expansion compatible with said insulating material of said container and having an acceptance portion for and being intimately sealed thereat by brazed connection with said container surface attachment region and having an internal channel extending along the lengthwise extent thereof,
   a lead connected in electrical contact with the apex of said conical insert and insulatively extending therefrom through said internal channel, and
   positioning and signal transfer means for operatively supporting said sleeve means and conveying electrical signals from said lead.

2. The electrode of claim 1 in which said positioning and signal transfer means comprises:
   a transition component formed of a select metal and having an internal channel extending therethrough to a sealing end and sealably connected with said sleeve means,
   said lead extending into the internal channel of the transition component, and
   cable connector means having a collar attached and sealed to said transition component sealing end and having a conductor extending therethrough for connection with the lead.

3. The electrode of claim 2 wherein said transition component is formed of stainless steel and is welded to said sleeve means to form a continuous internal channel from said internal channel of the transition component and the internal channel of said sleeve means.

4. The electrode of claim 3 wherein said sleeve means is comprised of Kovar.

5. The electrode of claim 1 wherein the insulator of said container comprises alumina.

6. The electrode of claim 5 wherein the alumina comprises sapphire.

7. The electrode of claim 1 wherein the sleeve means is comprised of Kovar.

8. The electrode of claim 1 wherein the lead is comprised of platinum.

9. The electrode of claim 1 wherein the metal-salt electrochemical reactant comprises AgCl.

10. The electrode of claim 1 wherein the conical insert comprises alumina.

11. The electrode of claim 1 wherein the conical insert comprises sapphire.

12. A container for electrochemical reactants for an electrode comprising a generally cylindrical member of an insulator, said member having a base region with an externally disposed surface attachment region and sidewall means extending to an access opening therefrom for defining an internally disposed cavity for containing said electrochemical reactants, means defining a generally conical cut-out in said base region that extends through said base region, and a generally conical cut-out, said insert, cut-out, and surface attachment region being metallized for acceptance of a silver braze, and said generally conical insert being set in place in said generally conical cut-out by silver brazing.

13. The container of claim 12 wherein the insulator of said member and of said insert comprises alumina.

14. The container of claim 12 wherein the insulator of said member and said insert comprises sapphire.

15. A reference electrode for employment within a fluid media and having an electrode system involving a metal/metal ion couple, comprising:

a generally cylindrical alumina container having a base region with an externally disposed surface attachment region and sidewall means extending to an access opening therefrom for defining an internally disposed cavity, means defining a conical cut-out in said base region that extends through said base region, a generally conical alumina insert that mates with said generally conical cut-out, said insert, cut-out, and surface attachment region being metallized for acceptance of a silver braze, said generally conical insert being set in place in said conical cut-out by silver brazing, a silver chloride electrochemical reactant located within said cavity, cap means formed of alumina and positioned over said container opening for retaining the silver chloride within said cavity while permitting electrolytic communication with said fluid media, sleeve means formed of Kovar exhibiting a coefficient of expansion compatible with said alumina of said container having an acceptance portion for and being intimately sealed thereat by silver brazed connection with said container surface attachment region and having a first internal channel extending along the lengthwise extent thereof, a platinum, lead connected in electrical contact with the apex of said conical insert and insulatively extending therefrom through said first internal channel, and a transition component formed of stainless steel and having a second internal channel extending therethrough to a sealing end and sealably connected with said sleeve means, said lead extends into the second internal channel of the transition component, and cable connector means having a metal collar attached and sealed to said transition component sealing end and having a conductor extending therethrough for connection with the lead.

16. The reference electrode of claim 15 wherein the container and conical insert is comprised of sapphire.

17. The reference electrode of claim 15, including an alumina tube located within said first and second channels through which said conductor extends for effecting the insulation thereof.

18. The reference electrode of claim 15 in which said alumina container externally disposed surface attachment region is nestably positioned within said sleeve means acceptance portion and is sealed thereto with a silver braze.

19. The reference electrode of claim 15 in which said insert, cut-out, and surface attachment region is metallized by providing a sequence of coatings, including a fired, metallized surface coating which is covered with a sintered nickel plate, over which is formed a sintered silver plate.

20. The reference electrode of claim 15 in which said sleeve means is covered with a sintered nickel plate coating.

* * * * *